(12) United States Patent
Gärber

(10) Patent No.: US 10,602,954 B2
(45) Date of Patent: Mar. 31, 2020

(54) DEVICE FOR PROCESSING AND VISUALIZING DATA OF AN ELECTRICAL IMPEDANCE TOMOGRAPHY APPARATUS FOR DETERMINING AND VISUALIZING REGIONAL PROPERTIES OF PULMONARY VENTILATION

(71) Applicant: Drägerwerk AG & Co. KGaA, Lübeck (DE)

(72) Inventor: Yvo Gärber, Breitenfelde (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 345 days.

(21) Appl. No.: 15/705,832

(22) Filed: Sep. 15, 2017

(65) Prior Publication Data

US 2018/0078168 A1    Mar. 22, 2018

(30) Foreign Application Priority Data

Sep. 16, 2016   (DE) .................. 10 2016 011 161

(51) Int. Cl.

| | |
|---|---|
| G06K 9/00 | (2006.01) |
| A61B 5/053 | (2006.01) |
| A61M 16/00 | (2006.01) |
| A61B 5/08 | (2006.01) |

(Continued)

(52) U.S. Cl.
CPC .......... *A61B 5/0536* (2013.01); *A61B 5/0809* (2013.01); *A61M 16/01* (2013.01); *A61M 16/024* (2017.08); *A61B 5/4836* (2013.01); *A61M 2205/3303* (2013.01); *A61M 2205/502* (2013.01); *A61M 2205/584* (2013.01); *A61M 2230/40* (2013.01); *A61M 2230/46* (2013.01); *A61M 2230/65* (2013.01)

(58) Field of Classification Search
None
See application file for complete search history.

(56) References Cited

U.S. PATENT DOCUMENTS

| | | |
|---|---|---|
| 5,807,251 A | 9/1998 | Wang et al. |
| 6,236,886 B1 | 5/2001 | Cherepenin et al. |
| 8,321,007 B2 | 11/2012 | Teschner et al. |

(Continued)

FOREIGN PATENT DOCUMENTS

| | | |
|---|---|---|
| EP | 1 292 224 B2 | 12/2009 |
| JP | 2002-531207 A1 | 9/2002 |

(Continued)

OTHER PUBLICATIONS

Notice of Reason for Rejection dated Aug. 15, 2018 during the examination of Japanese Patent Application No. 2017-178076 with machine translation.

(Continued)

*Primary Examiner* — Atiba O Fitzpatrick
(74) *Attorney, Agent, or Firm* — McGlew and Tuttle, P.C.

(57) ABSTRACT

A great device (10) processes and visualizes electrical impedance tomography (EIT) data (3) of at least one region of the lungs for determining and visualizing regional properties of the lungs of a living being. The EIT data (3) are obtained from an electrical impedance tomography apparatus (30). The device makes it possible to visualize regional properties of the lungs or of regions of the lungs in terms of hyperdistension or collapse.

17 Claims, 1 Drawing Sheet

(51) Int. Cl.
  *A61M 16/01* (2006.01)
  *A61B 5/00* (2006.01)

(56) References Cited

U.S. PATENT DOCUMENTS

| | | |
|---|---|---|
| 2010/0228143 A1 | 9/2010 | Teschner et al. |
| 2014/0100436 A1* | 4/2014 | Brunner ............... A61N 1/0476 |
| | | 600/372 |
| 2014/0155732 A1* | 6/2014 | Patz ..................... A61B 5/055 |
| | | 600/410 |
| 2015/0238115 A1 | 8/2015 | Nonaka |
| 2016/0339191 A1* | 11/2016 | Kaczka ............... A61M 16/203 |
| 2019/0125277 A1* | 5/2019 | Radke ................. A61M 16/026 |

FOREIGN PATENT DOCUMENTS

| | | |
|---|---|---|
| JP | 2012-061057 A | 3/2012 |
| JP | 2015-160005 A1 | 9/2015 |
| WO | 0033733 A1 | 6/2000 |

OTHER PUBLICATIONS

"Tidal recruitment assessed by electrical impedance tomography and computed tomography in a porcine model of lung injury" [Critical Care Med, 2011, vol. 40, No. 3].

"Bedside estimation of recruitable alveolar collapse and hyperdistension by electrical impedance tomography" [Intensive Care Med, 2009].

* cited by examiner

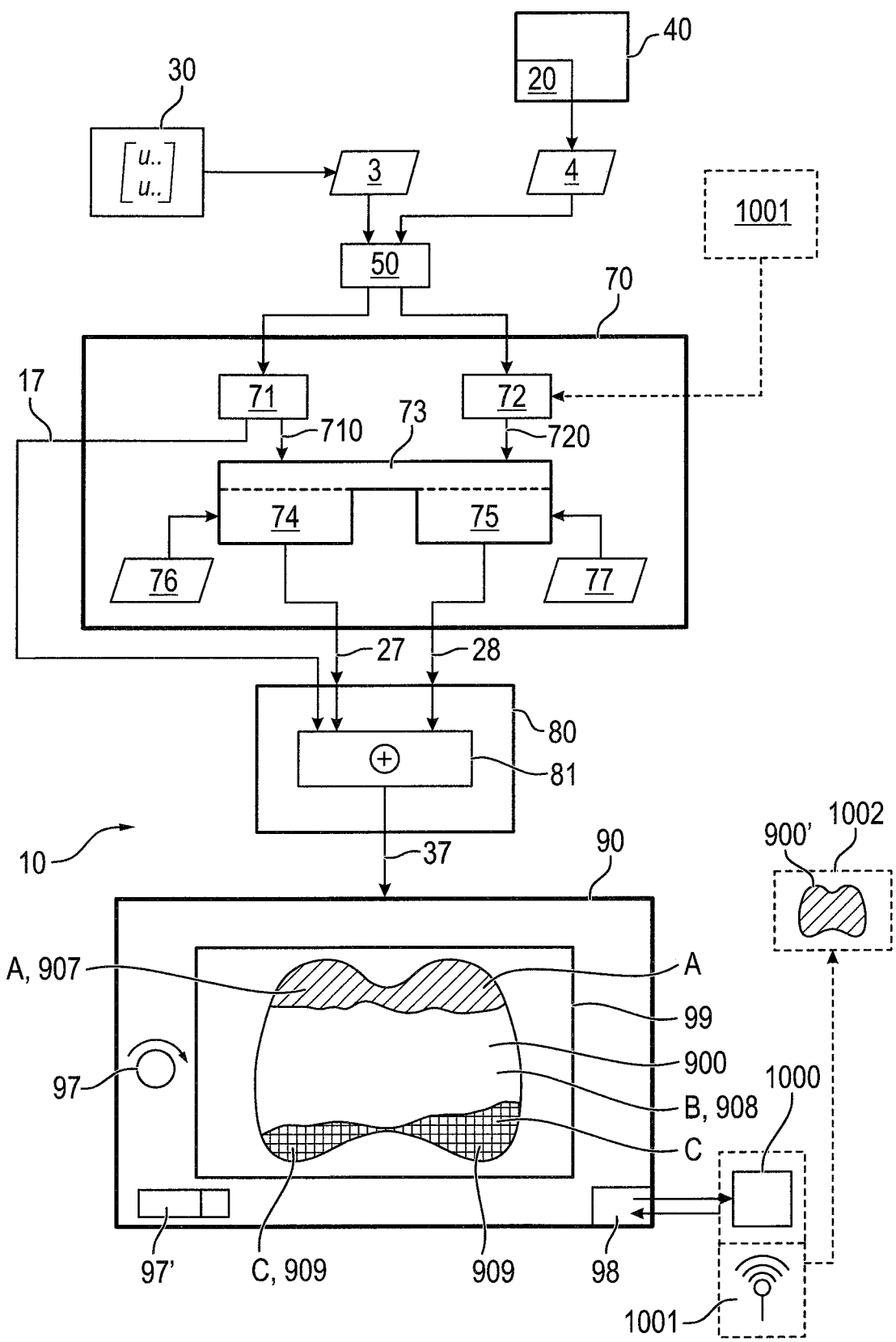

DEVICE FOR PROCESSING AND VISUALIZING DATA OF AN ELECTRICAL IMPEDANCE TOMOGRAPHY APPARATUS FOR DETERMINING AND VISUALIZING REGIONAL PROPERTIES OF PULMONARY VENTILATION

CROSS REFERENCE TO RELATED APPLICATIONS

This application claims the benefit of priority under 35 U.S.C. § 119 of German Application 10 2016 011 161.5, filed Sep. 16, 2016, the entire contents of which are incorporated herein by reference.

FIELD OF THE INVENTION

The present invention pertains to a device for processing and visualizing data of an electrical impedance tomography (EIT) apparatus for determining and visualizing regional properties of the pulmonary ventilation of a living being.

The device according to the present invention makes possible a special form of visualizing lung regions, whose properties in terms of lung compliance during the ventilation vary relative to a comparison variable.

BACKGROUND OF THE INVENTION

On the one hand, regions with given hyperdistensions of individual lung regions or pulmonary air cells (alveoli) as well as regions of the lungs in which the pulmonary alveoli have collapsed into themselves, i.e., there are collapses of individual lung regions or pulmonary air cells (alveoli), can be mentioned as lung regions with associated properties.

Apparatuses for electrical impedance tomography are known from the state of the art and are configured and intended for generating an image, a plurality of images or a continuous sequence of images from signals obtained by means of electrical impedance measurements and from data and data streams obtained from such signals. These images or sequences of images show differences in the conductivity of different tissues of the body, such as bones, skin, body fluids and organs, especially the lungs, which are useful for observing the situation of a patient.

Thus, U.S. Pat. No. 6,236,886 describes an electrical impedance tomography apparatus with an array of a plurality of electrodes, a power input at at least two electrodes, a signal acquisition unit at the other electrodes and a method with an algorithm for image reconstruction for determining the distribution of conductivities of a body such as bones, skin and blood vessels in a schematic embodiment with components for signal acquisition (electrodes), signal processing (amplifiers, A/D converters), power input (generator, voltage-to-current converter, current limitation) and components for control functions.

It is explained in U.S. Pat. No. 5,807,251 that it is known in the clinical application of EIT that a set of electrodes is provided as an electrode ring, which set is arranged around the chest of a patient such that its electrodes are spaced at a defined distance from one another in electrical contact with the skin. An electrical current or voltage input signal is applied alternatingly between different electrode pairs or between all of the possible electrode pairs of electrodes arranged adjacent to one another. While the input signal is applied to one of the pairs of electrodes arranged adjacent to one another, the currents or voltages between each pair of the other electrodes, which said pairs are adjacent to one another, are measured, and the data obtained are processed, in order to obtain a visualization of the distribution of the specific electrical resistance over a cross section of the patient, around whom the electrode ring is arranged, and to display this on a display screen.

Unlike other imaging radiological methods (X-ray apparatuses, radiological computed tomographs), electrical impedance tomography (EIT) has the advantage that no radiation burden harmful for the patient occurs. Contrary to sonographic methods, continuous image acquisition can be performed with EIT over a representative cross section of the entire thorax and of the lungs of the patient by means of the electrode belt.

In particular, it is possible by means of EIT to make it graphically possible, in a so-called "tidal image" in the transverse plane of the body, to obtain a visualization of the lungs, showing which regions of the lungs are currently well ventilated and which regions of the lungs are ventilated less well, because the impedances of well ventilated and less well ventilated lung regions differ markedly from one another.

Measured value acquisition of the electrode signals at a scanning rate that makes possible a reconstruction of a sequence of images in order to resolve in time individual breaths, especially the inhalation phases and exhalation phases of a breath, is a basic requirement for analyzing regional distributions of the ventilated air. It is thus possible both to analyze the regional distribution of the ventilated air in the end-inspiratory state and in the end-expiratory state and to examine the characteristics over time during the inhalation and during the exhalation in order to infer lung-mechanical effects, processes and events in the different regions of the lungs.

Lung-mechanical processes and events are, for example, inflow or outflow characteristics of the air caused by flow resistances in the airways and bronchi or bronchioli and alveoli as well as redistributions between different lung regions during the course of the inhalation or exhalation.

Further lung-mechanical effects arise, for example, in case of an excessively high ventilation pressure as well as in case of an excessively low ventilation pressure, so that alveoli are collapsed in some lung regions due, on the one hand, to an excessive distension, (overdistension, hyperdistension, pulmonary emphysema), and, on the other hand, alveoli are collapsed due to an insufficient opening pressure, so that these alveoli are not available for the gas exchange of oxygen and carbon dioxide with the blood circulation.

An example of regional lung-mechanical processes and events is described in the scientific article "Tidal recruitment assessed by electrical impedance tomography and computed tomography in a porcine model of lung injury" [Critical Care Med, 2011, Vol. 40, No. 3]. Different forms of ventilation, such as pressure-controlled ventilation or volume-controlled ventilation, show, together with the settings of the ventilation parameters to be adapted to the patient, such as tidal volume (Vt), respiration rate (RR), inhalation to exhalation ratio (I:E ratio), inhalation pause and exhalation pause, inspiratory pressure (Pinsp), positive end-expiratory pressure (PEEP), a difference in how the breathing gas flows into different regions of the lungs in the course of inhalation over time. Thus, there may be situations in which some regions of the lungs may be hyperdistended, while the opening pressure is too low for some alveoli to open these alveoli and to end the state of collapse in other regions of the lungs at nearly the same time.

The possible effects on the gas exchange are described in the scientific article "Tidal recruitment assessed by electrical impedance tomography and computed tomography in a porcine model of lung injury" [Critical Care Med, Vol. 40, No. 3] that the manner of ventilation thus induces delays in the gas exchange of lung regions, which are due to the so-called "tidal recruitment." "Tidal recruitment" describes a state of lung regions in which individual collapsed alveoli or a plurality of collapsed alveoli open with a delay only as the pressure increases compared to the other regions of the lungs and close, i.e., collapse again, in turn, prematurely as the ventilation pressure decreases during the exhalation.

How, when and which regions of the lungs are affected by "tidal recruitment" are affected by the settings of the ventilation pressure and of the ventilation pressure curve. Consequently, both a shortened inhalation time and a shortened exhalation time are obtained for these individual collapsed alveoli or for this plurality of collapsed alveoli compared to other regions of the lungs.

Visualization of hyperdistended and collapsed regions of the alveoli (air cells) is advantageous for setting the ventilation parameters and continuously controlling the ventilation parameters. It is described in the scientific article "Bedside estimation of recruitable alveolar collapse and hyperdistension by electrical impedance tomography" [Intensive Care Med, 2009] with respect to the ventilation parameters in terms of the hyperdistension and collapse how regions of the lungs, in which states of excessive distension (hyperdistension) and/or collapse occur, can be identified by means of a simultaneous application of electrical impedance tomography (EIT) and radiological computed tomography (CT). Including values of the ventilation pressure, an image of the best possible or maximum compliance, i.e., the compliance of individual lung regions, is determined for this by means of specific maneuvers with a stepwise reduction of the positive end-expiratory ventilation pressure (PEEP trial) at defined times, at the end of the phase of inhalation and of the phase of exhalation. Compliance is defined in medicine as the quotient of the change in volume to the change in pressure. The unit of measurement is L/kPa, and the unit mL/cm $H_2O$ is also frequently used in medicine as well. The impedances or impedance changes determined by means of EIT are used as the equivalent for the change in volume in the electrical impedance tomographic determination of hyperdistension and collapse.

EP 1 292 224 B2 describes a method and a device for the visualization of data which were obtained by means of electrical impedance tomography. Different special modes of analysis, on the basis of which an analysis of the state of the lungs of a patient is intended, are described. Thus, a relative mode is provided, which processes regional changes in a two-dimensional distribution of the ventilation for a past time period, and a phase-shifting mode is used to process the dynamics of ventilation. Furthermore, a perfusion mode is provided, which generates a two-dimensional distribution of the lung perfusion. Further modes described in this EP 1 292 224 B2 are the absolute mode, the time constant mode and a regional spirometry mode. The different modes are used to distinguish different states of the lungs.

It is common to all the modes described in this EP 1 292 224 B2 that no modes and no combination of modes are provided that would make possible a joint visualization of regionally different states of the lungs, such as hyperdistension or collapse.

SUMMARY OF THE INVENTION

Considering the knowledge of the above-described drawbacks of the known prior art, an object of the present invention is to provide a device that makes it possible to determine regional and different properties of the lungs from EIT data and to combine these different and regional properties in a joint visualization.

According to the invention, a device is provided for processing and visualizing electrical impedance tomography data of at least one region of lungs for determining and visualizing properties of the lungs. The device is based on the EIT data being obtained by means of an electrical impedance tomography apparatus. The device comprises a data input unit configured to receive and provide the EIT data of the at least one region of the lungs over an observation period and to receive and provide data indicating a change in a ventilation pressure during the observation period. The device also comprises a calculation and control unit configured to determine local impedance values and impedance changes of at least one region of the lungs from the EIT data, to determine a data set with regional properties of the lungs, which indicates an indicator of compliance of the lungs, from the local impedances and local impedance changes, taking into account data that indicate a change in a ventilation pressure during the observation period, to analyze the data set with regional properties of the lungs based on a first comparison criterion to determine whether these properties indicate a hyperdistension of regional regions of the lungs, to generate and provide a regional hyperdistensions control signal, which represents the local regions of the lungs, with regional properties indicative of regional hyperdistensions, to analyze the data set with the regional properties of the lungs based on a second comparison criterion to determine whether these properties indicate a collapse of regional regions of the lungs and to generate and provide a regional collapses control signal, which represents the local regions of the lungs, whose regional properties indicate regional collapses. The device further comprises an output unit configured to generate, provide or output an output signal using the regional hyperdistensions control signal and the regional collapses control signal, wherein the output signal represents a profile of properties for a visualization of local regions of the lungs, with regional properties showing deviations from the first comparison criterion or from the second comparison criterion.

Some of the terms used within the framework of this disclosure will be explained more specifically at the beginning.

An observation period is defined in the sense of the present invention as a time period in a time course. The beginning and the end of such an observation period are defined either by fixed or adaptable times or by events that are given by the properties of breathing or ventilation. Examples of observation periods that are based on breathing or ventilation are a breathing cycle, a plurality of breathing cycles, parts of breathing cycles such as inhalation, inspiratory pause, exhalation, expiratory pause. Other observation periods, especially in case of mechanical ventilation, may be periods with defined pressure levels, such as plateau pressure, PIP pressure (positive inspiratory pressure, PIP) or PEEP pressure (positive end expiratory pressure, PEEP), PIP or PEEP pressure stages, ascending or descending PIP pressure ramps or PEEP pressure ramps as part of a special ventilation maneuver or time periods that correspond to certain properties of forms of ventilation (e.g., Bi-Level Positive Airway Pressure, BiPAP).

Measured EIT signals are defined in the sense of the present invention as signals or data that can be acquired with an EIT apparatus by means of a group of electrodes or by means of an electrode belt. These include measured EIT signals with different signal characteristics, such as electrical voltages or measured voltage signals, electrical currents or measured current signals, assigned to electrodes or to groups of electrodes or to positions of electrodes or of groups of electrodes on the belt, as well as resistance or impedance values derived from voltages and currents.

A measurement cycle is defined in the sense of the present invention as a sequence of feeds at a plurality of feeding electrode pairs with a respective corresponding measuring run on other electrodes. Such a measurement cycle is typically called a so-called "frame" or "time frame" in connection with the processing of EIT data. A measurement cycle is composed of a plurality of measuring runs. A measuring run is defined in the sense of the present invention as a signal feed on two feeding electrodes, on a so-called feeding electrode pair, during which acquisitions of measured EIT signals are performed on other electrodes different from these two feeding electrodes. A measuring run as a part of a measurement cycle is correspondingly typically called a "partial frame" in connection with the processing of EIT data.

A control signal is defined in the sense of the present invention as an individual control signal, a control signal as part of a set of control signals, as well as a plurality of control signals or as a set of control signals.

An output signal is defined in the sense of the present invention as an individual output signal, as an output signal as part of a set of output signals, as well as a plurality of output signals or as a set of output signals.

A tidal image of the lungs is defined in the sense of the present invention as an image that corresponds, at a defined time, spatially resolved, to a visualization of a distribution of local impedances in a transverse view of the lungs. The impedances are determined continuously in the measurement cycle. The local impedances represent the degree of filling of local areas of the lungs with air in the rhythm of inhalation and exhalation. The tidal image is visualized in the usual manner of visualization in a horizontal section plane through the thorax of a living being in a so-called dorsal view.

A plurality of tidal images of the lungs in a temporal sequence, for example, as a sequence of images or film (video), represent the changes in the impedances and hence changes over time in the ventilation of individual local lung regions.

For processing and visualizing EIT data obtained by means of an electrical impedance tomography apparatus suitable for generating data for imaging for at least one region of the lungs or thorax, the device according to the present invention has a data input unit, a calculation and control unit, and an output unit.

The data input unit is configured to receive and provide EIT data of at least one region of the lungs or thorax. The EIT data represent for a plurality of lung regions regional ventilation situations of the lungs for at least one location of the lungs over an observation period. A typical observation period is an EIT acquisition period, which comprises a plurality of measurement cycles (time frames, partial frames) with EIT data.

The data input unit is further configured to receive and provide measured pressure values from a ventilation course, which are provided, for example, by an anesthesia apparatus or ventilator.

The data input unit is further configured to receive and provide data, which are provided, for example, for a physiological monitor, medical therapy and treatment device, preferably an anesthesia apparatus or ventilator.

The data input unit is optionally preferably configured, furthermore, for receiving and providing data of a ventilation control, which are provided by a medical therapy or treatment device, preferably by an anesthesia apparatus or ventilator.

The data input unit preferably has for this interface components, for example, level converters, amplifiers, A/D converters, components for overvoltage protection, logic components and additional electronic components for the wired or wireless reception of the data and signals as well as adaptation components, such as code or protocol conversion components for adapting the signals and data for the further processing in the calculation and control unit.

The calculation and control unit is configured to determine local impedances and local impedance changes of at least one region of the lungs from the EIT data, to determine a data set with regional properties of the lungs, which properties indicate an indicator for the compliance of the lungs, from the local impedance values and local impedance changes, taking into account provided data, which indicate changes in a ventilation pressure during the observation period, to analyze the data set with the determined regional properties of the lungs on the basis of a first comparison criterion to determine whether these properties indicate a hyperdistension of regional lung regions, to generate and provide a second control signal (regional hyperdistensions control signal), which represents the local regions of the lungs, whose regional properties indicate regional hyperdistensions, to analyze the data set with the regional properties determined on the basis of a second comparison criterion to determine whether these properties indicate a collapse of regional lung regions, and to generate and provide a third control signal (regional collapses control signal), which represents the local lung regions, whose regional properties indicate regional collapses.

The determination of the regional properties of the lungs is carried out by means of the calculation and control unit in such a manner that impedances or impedance changes of at least one region of the lungs are determined from EIT data, which are provided by an EIT apparatus. The EIT data are usually provided as measured voltage values or measured current values. The present invention also covers the case in which the calculation and control unit may be configured as a part of an EIT apparatus.

Furthermore, the data, which indicate the changes in a ventilation pressure during the observation period, are taken into account by the calculation and control unit.

The determination of the regional properties of the lungs is carried out according to the present invention in reference to the comparison criteria, which are related to the observation period and indicate "best possible compliances" of the lung regions in respective individual regions of the lungs.

A plurality of exhalation phases as an observation period with mutually different values of a positive end-expiratory pressure (PEEP) as steps of a maneuver with changes in the ventilation pressure are preferably used as data that indicate the course of the ventilation pressure. Local impedances and local impedance changes, which are determined from respective EIT data and correspond to the mutually different values of the positive end-expiratory pressure (PEEP), are available for these values to determine the respective indicator of the compliance for local lung regions.

An advantageously suitable maneuver for generating mutually different steps of the positive end-expiratory pressure (PEEP) is the so-called PEEP trial, in which, beginning from a starting value, the ventilation pressure, i.e., the pressure level of the positive end-expiratory pressure (PEEP), to which the ventilation pressure drops each time at the end of the exhalation, is increased in steps (incremental PEEP trial) or is decreased (decremental PEEP trial).

The second control signal and the third control signal are used in the output unit to generate, provide or output an output signal. The output signal represents a profile of properties for the visualization of local lung regions, that has regional properties that show deviations from the first comparison criterion or from the second comparison criterion.

The output signal is thus representative of the profile of properties of the respective properties of one or more lung regions, whose regional properties indicate regional collapses or regional hyperdistensions.

It advantageously follows from this, when this output signal is used for an output in a joint visualization, that both lung regions with hyperdistension and lung regions with collapse are visible at the same time in the joint visualization.

In addition to components that represent the regional property, the output signal may also have, in the sense of the present invention, information components that make it possible to highlight local regions by shading, with colors, graphic coding on the basis of gray tints, brightness levels, color transparency or saturation levels or patterns and can thus be displayed by the data output unit pictorially, graphically and/or visually.

This advantageously increases the analyzability of the visualization, because the local lung regions of special interest, namely, the local lung regions in which collapses or hyperdistensions are present, become prominently visible in the joint visualization. This has the advantage that the user gains a prepared view of the regional properties with essential relevance for an estimation of the ventilation situation of the lungs in respect to regional properties in terms of hyperdistension and collapse in a single, joint visualization simultaneously and at the same time in a mutually directly distinguishable manner, without changes in two visualizations of hyperdistension and collapse, visualized independently from one another, having to be visually and cognitively acquired simultaneously.

This makes it possible for the downstream output unit to visualize the essentially non-collapsed as well as the non-hyperdistended lung regions with a color scale of blue with light blue to white as a graphic gradation for a degree of ventilation and the regional properties of collapses and hyperdistensions with different color scales, for example, with a reddish color scale with dark red to light red for hyperdistensions and with a brownish color scale from light brown to dark brown for regions with collapses as graphic gradations, for different grades of hyperdistension or collapse.

To carry out the described tasks of the calculation and control unit, the calculation and control unit has components for data processing, calculation and process control, such as microcontrollers (µC), microprocessors (µP), signal processors (DSP), logic components (FPGA, PLD), memory components (ROM, RAM, SD-RAM) and combination variants thereof, for example, in the form of an "embedded system," which are configured with one another and adapted to one another or are configured by programming for carrying out the necessary steps for processing and visualizing data obtained by means of an EIT apparatus suitable for generating data for imaging to determine regional properties of the lungs and for processing an output signal for visualizing the profile of properties of the lungs.

The output unit is configured as an image processing and data output unit to output, provide or visualize regional properties of the lungs with the use of the output signal.

The output unit is configured to generate, provide or visualize the output signal. The output signal is preferably configured as a video signal (e.g., Video Out, Component Video, S-Video, HDMI, VGA, DVI, RGB) to make possible a graphic, numeric or pictorial visualization of the regional properties of the lungs on a display unit connected to the output unit in a wireless or wired manner (WLAN, Bluetooth, WiFi).

In a preferred embodiment, the calculation and control unit is configured to determine local impedances and local impedance changes from the EIT data and to determine a tidal image of a current distribution of the impedance values and impedance changes in the lungs from the determined local impedances and local impedance changes and to generate and provide a first control signal (tidal image control signal), which is representative of the determined, current tidal image of the lungs.

In a preferred embodiment, a data output unit with a component for graphic visualization is arranged on or connected to the device for processing and visualizing EIT data. The component for graphic visualization is configured for visualization with the use of the output signal.

The visualization of the determined tidal image and/or of the profile of properties by means of the one component for graphic visualization is now carried out with the use of the first control signal or of the second control signal and/or of the third control signal and/or of the output signal. The visualization may preferably take place by means of the component for graphic visualization in a combined visualization of the tidal image and the profile of properties. A combined visualization by means of the component for graphic visualization may preferably be configured, for example, as a horizontally or vertically split display on a screen (split screen) or as an optional, as well as overlapping or superimposed arrangement of display windows on the screen.

In a preferred embodiment, values, which indicate positive end-expiratory pressure values (PEEP) in the observation period, are determined by the calculation and control unit on the basis of the data that indicate measured pressure values of the course of ventilation.

In another preferred embodiment, data sets with maximum regional compliances are determined in the observation period for a plurality of local regions of the lungs by the calculation and control unit on the basis of the regional properties, which indicate the compliance, and on the basis of the data that indicate the measured pressure values of the ventilation course and/or from the positive end-expiratory pressure values (PEEP).

In another preferred embodiment, the first comparison criterion is determined in the observation period by the calculation and control unit on the basis of the data sets of maximum compliances and of the values that indicate positive end-expiratory pressure values (PEEP).

In another preferred embodiment, the second comparison criterion is determined by the calculation and control unit in the observation period on the basis of the data sets of maximum compliances and of the values that indicate positive end-expiratory pressure values (PEEP).

In another preferred embodiment, the duration of at least two breathing cycles with respective inhalation phases and expiration phases is selected as the period.

In another preferred embodiment, the duration of a maneuver with changes in the ventilation pressure, preferably decremental or incremental PEEP trials with a plurality of breathing cycles with respective inhalation phases and exhalation phases is selected as the observation period.

In another preferred embodiment, the data are provided by a ventilator or anesthesia apparatus.

If the data are provided by a ventilator or anesthesia apparatus, the data may contain, for example, data that indicate tidal volumes (Vt), respiration rate (RR), inhalation to exhalation ratio (I:E ratio), inspiratory and expiratory pauses, inspiratory pressure (Pinsp), positive end-expiratory pressure: PEEP). Times and corresponding pressure values in the course of the ventilation, such as the end of inhalation and end of exhalation, as well as the start of exhalation or start of inhalation, can be determined from this by the calculation and control unit.

In another preferred embodiment, the device for determining and visualizing properties of the lungs is configured as a device or combination of devices with functions for carrying out a ventilation and/or for carrying out an anesthesia, for carrying out an impedance tomography (EIT) and with functions for determining and visualizing properties of the lungs.

The present invention will be explained in detail now by means of FIG. 1 below and of the corresponding description of the FIGURE without limitations of the inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:
FIG. 1 is a schematic view of a device for processing and visualizing data with pictorial visualization of regional properties of collapse and hyperdistension.

DESCRIPTION OF THE PREFERRED EMBODIMENTS

Referring to the drawings, FIG. 1 shows a device 10 for processing and visualizing data. The device 10 has as essential components a data input unit 50, a calculation and control unit 70, an image processing and output unit 80 as well as a data output unit 90.

EIT data 3 are transmitted or sent from an EIT apparatus 30 to the calculation and control unit 70 by means of the data input unit 50. The EIT data 3 are processed further in the calculation and control unit 70. After receipt of the EIT data 3, local impedance values 710 of the lungs are calculated in an impedance calculation unit 71, which is present in the calculation and control unit 70. Impedance values 710 of different local regions of the lungs, which make it possible to visualize the distribution of the impedances in the lungs of a living being on the basis of the EIT data 3 obtained with the EIT apparatus 30, are calculated. The impedances represent different degrees of ventilation or quality of ventilation of lung regions.

The impedance values 710 obtained with the impedance calculation unit 71 and impedance changes represent a tidal image of the lungs and are provided as a first control signal (tidal image control signal) 17 to an image processing unit 81 in the image processing and output unit 80 for further data processing.

Pressure values 20 are transmitted or sent as measured or operating data 4 of the ventilator 40 from a ventilator 40 to a data supply unit 72 arranged in the calculation and control unit 70 by means of the data input unit 50. The measured or operating data 4 are processed in the calculation and control unit 70 by a data consolidation unit 73 and provided to and are processed further by a first property determination unit 74 and by a second property determination unit 75 together with the impedance values 710. As an alternative, the operating data 4 may be fed, also in connection with additional data, to the data supply unit 72 indirectly through a data network 1001, e.g., through a LAN or via an Intranet or other data network in the hospital.

The data consolidation and data processing unit 73 is configured and intended to determine a data set of local end-expiratory impedance values of the lungs in relation to the measured or operating data 4, which are or have been obtained, for example, from different degrees of a positive end-expiratory pressure (PEEP) obtained by means of a maneuver performed by the ventilator during a so-called PEEP trial, and to provide them as a processed data set with local values 720, which indicate positive end-expiratory pressure values (PEEP).

The mathematical procedure employed for an area (pixel) of the lungs as follows.

An indicator of the lung compliance, the so-called "compliance," is determined as a quotient of the local impedance changes 71 and the corresponding PEEP value from the decremental PEEP trial, i.e., stepwise reductions of the PEEP level from a starting value.

The starting value of the PEEP value is selected here such that this value is just high enough to be able to assume at this value, on average, a slight hyperdistension of the lungs. A so-called "best compliance" is selected for each local lung region, i.e., a value at which the ratio of the pressure applied to ventilate the lung region is especially advantageous, i.e., the positive end-expiratory pressure (PEEP) is selected to be just high enough for the lung region, i.e., the alveoli, to distend maximally and thus to have a maximum surface for an optimal local gas exchange between the blood circulation and the breathing gas in the lung region, without being hyperdistended by an excessively high pressure. The "best compliance" is determined, for example, by the fact that the value starting from which a less favorable indicator of compliance can be calculated as a quotient due to a further pressure reduction is determined as "best compliance" in the decremental course of the PEEP trial. Reference is made here in connection with the determination of "compliance" and "best compliance" to the scientific article "Bedside estimation of recruitable alveolar collapse and hyperdistension by electrical impedance tomography" [Intensive Care Med 2009], which was already mentioned above (and is incorporated herein by reference).

The local indicators of compliance determined for the different PEEP levels are subsequently related for the local regions to the "best compliance." This is accomplished by the first property determination unit 74, in the calculation and control unit 70, being provided for determining a first property, which indicates hyperdistensions, on the basis of a first comparison criterion 76. In addition, the second property determination unit 75, in the calculation and control unit 70, is intended for determining a second property, which indicates collapses, on the basis of a second comparison criterion 77.

The first comparison criterion and the second comparison criterion are derived from the "best compliance," e.g., 10% above and 10% below the "best compliance" or identically to the "best compliance."

If such a PEEP trial is advantageously carried out during a pressure-controlled ventilation as a decremental PEEP trial with a plurality of PEEP levels beginning from a known pressure level with constant and predefined pressure differences between the PEEP levels, the mathematical procedure becomes simpler, so that the pressure differences of the different PEEP levels can be eliminated from the formulas for calculation hyperdistension or collapse. Reference is made here concerning the mathematical relationships for determining "compliance," "best compliance," "collapse" as well as "hyperdistension" to the scientific article "Bedside estimation of recruitable alveolar collapse and hyperdistension by electrical impedance tomography" [Intensive Care Med 2009], which was already mentioned above.

The following formulas 1, 2, 3a, 3b are used only for a simplified illustration for eliminating the pressure difference $\Delta P$ by using formula 1 in formula 2 when determining the indicator (compliance) of hyperdistension and collapse at a constant pressure difference $\Delta P$, as it is made possible by performing the PEEP trial with constant steps $\Delta P$ of the pressure change, by means of formula 3b. Formula 3a shows the intermediate mathematical step of mathematically eliminating the pressure difference $\Delta P$.

$$\text{Compliance} = \frac{\Delta Z}{\Delta P} \quad \text{Formula 1}$$

$$\text{best\_compliance} = \frac{\text{best compliance} - \text{current\_compliance}}{\text{best compliance}} \quad \text{Formula 2}$$

$$\text{best\_compliance} = \frac{\frac{\Delta Z_{best\ compliance}}{\Delta P} - \frac{\Delta Z_{current\ compliance}}{\Delta P}}{\frac{\Delta Z_{best\ compliance}}{\Delta P}} \quad \text{Formula 3a}$$

$$\text{best\_compliance} = \frac{\Delta Z_{best\ compliance} - \Delta Z_{current\ compliance}}{\Delta Z_{best\ compliance}} \quad \text{Formula 3b}$$

It is thus possible, without knowledge of the particular absolute value of the pressure differences $\Delta P$ between the individual PEEP steps, to determine the properties of local lung regions from the impedance values 710. It is only necessary that information that indicates that the EIT data 3 provided were obtained during a PEEP trial be available to the calculation and control unit 70. Information on whether the PEEP trial was carried out decrementally or incrementally is helpful for the analysis, but is not absolutely necessary; this also applies in a comparable manner to the starting value as well as the start time.

Instead of the pressure differences $\Delta P$ between the individual PEEP steps, a so-called "DELI value" (Delta-End-expiratory Lung Impedance) may also be used as an equivalent value, especially for a PEEP trial carried out during pressure-controlled ventilation as a variant for a rough estimation, if no measured or operating data 4 of the ventilator 40 are available. It is only necessary for this that a PEEP trial shall have been carried out by the ventilator 40, so that from the estimation equidistant impedance changes 71 are obtained as DELI values from equidistant pressure differences $\Delta P$ in the acquired EIT data 3 nearly synchronously thereto.

The first property determination unit 74 determines local lung regions, which show a property of hyperdistension, on the basis of a first comparison criterion 76 and of the impedance values and impedance changes 710, taking into account the data set with local values 720, which indicate positive end-expiratory pressure values (PEEP), and generates a second control signal (regional hyperdistensions control signal) 27, which indicates the property of hyperdistension.

The second control signal 27 is provided to the image processing unit 81 in the image processing and output unit 80 for further data processing.

The second property determination unit 75 determines local lung regions that show the property of collapse on the basis of a second comparison criterion 77 and the impedance values and impedance changes 710, taking into account the data set with local values 720, which indicate positive end-expiratory pressure values (PEEP), and generates a third control signal (regional collapses control signal) 28, which indicates the property of collapse.

The third control signal 28 is provided to the image processing unit 81 in the image processing and output unit 80 for further data processing.

The first comparison criterion 76 and the second comparison criterion 77 are criteria that are derived from the "best compliance," wherein the first comparison criterion 76 indicates a state with greater distension or hyperdistension of the local lung region compared to the "best compliance" and wherein the second comparison criterion 77 indicates a state with reduced filling or distension of the local lung region compared to the "best compliance."

Provisions may be made in a special variant for the first comparison criterion 76 and the second comparison criterion 77 to be selected to be identical to one another, for example, as a state with greater distension compared to the "best compliance" or as a state with reduced filling of the local lung region compared to the "best compliance" or identically to a state of "best compliance" of the local lung region.

The image processing unit 81 generates an output signal 37 from the second control signal 27 and from the third control signal 28. This output signal 37 is representative of a pictorial visualization of information on a ventilation situation of local lung regions as a profile of properties 900 in a dorsal visualization view. Inclusion of the first control signal 17 in the output signal 37 can make possible, in an optional and advantageous embodiment, a combined visualization of the profile of properties 900 with the determined tidal image of the lungs, which tidal image represents the current ventilation of the lungs, e.g., in a form of a split display screen (split screen) or as an optional, as well as overlapping or superimposed arrangement of display windows on the display screen.

The output signal 37 is made available in this FIG. 1, as an example, to a data output unit 90 connected to the device 10. Different components are present in this data output unit 90. For example, a component for graphic visualization, e.g., a screen 99, is present. Furthermore, operating components 97, 97', such as keys 97' or rotary knobs 97, are arranged in the data output unit 90. Further, an interface 98 is optionally provided on the data output unit 90 for a data exchange, via with additional devices such has a bidirectionally connected data processing device 1000. Other connected devices especially include an external monitor 1002 or with the hospital data network 1001 (LAN, WAN, WLAN, Ethernet, WiFi), which are not shown more specifically in detail in FIG. 1.

The profile of properties 900 is displayed in the graphic visualization component 99. As an alternative or in addition, a profile of properties 900' may also be displayed on an external monitor 1002 connected to the device 10 via the data exchange by means of the data network 1001.

Lung regions in which hyperdistensions are identified are shown in the visualization of the lung contour as specially marked regions A, 907 and are graphically specially highlighted. Lung regions in which collapses are identified are shown in the visualization of the lung contour as specially marked regions C, 909 and are graphically specially highlighted. Lung regions in which neither collapses nor hyperdistensions are identified are shown in this FIG. 1 as a region B, 908.

The manners in which the markings A 907 and C 909 are made in the profile of properties 900 are advantageously mutually different, for example, by means of different texture or shading patterns (as is shown as an example in this FIG. 1) or they are also based on a variation of colors.

This has the advantage that the user gets a prepared view of the regional properties with essential relevance for an estimation of the ventilation situation. This prepared view facilitates the visual and cognitive detection of the ventilation situation to the user.

Instead of highlighting by shading, as is shown in FIG. 1, a visualization and highlighting may also be contained in the output signal 37 with colors, graphic coding or textures on the basis of gray tints, brightness levels, color transparency or saturation steps or patterns as information and thus displayed 99 graphically and visually for distinguishing the regions A907, B908 and C909.

While specific embodiments of the invention have been shown and described in detail to illustrate the application of the principles of the invention, it will be understood that the invention may be embodied otherwise without departing from such principles.

APPENDIX

List of Reference Designations

3 EIT data
4 Operating data of the ventilator
10 Device for processing and visualizing data
17 First control signal (tidal image)
20 Measured pressure values
27 Second control signal (hyperdistension)
28 Third control signal (collapse)
30 Electrical impedance tomography apparatus
37 Output signal
40 Ventilator
50 Data input unit
70 Calculation and control unit
71 Impedance calculation unit
72 Data supply unit
73 Data consolidation unit (pressure values/impedance values)
74 First property determination unit
75 Second property determination unit
76 First comparison criterion
77 Second comparison criterion
80 Image processing and data output unit
81 Image processing unit
90 Data output unit
97, 97' Operating components
98 Interface
99 Component for graphic visualization (screen)
710 Impedance values
720 Pressure values
900, 900' Profile of properties
907 Marked regions A (hyperdistensions)
908 Not specially marked region B
909 Marked regions C (collapses)
1000 Bidirectionally connected data processing device
1001 Data network, Intranet, Internet
1002 External monitor

What is claimed is:

1. A device for processing and visualizing electrical impedance tomography (EIT) data of at least one region of lungs for determining and visualizing properties of the lungs, wherein the EIT data are obtained by means of an electrical impedance tomography apparatus, the device comprising:
   a data input unit configured:
      to receive and provide the EIT data of the at least one region of the lungs over an observation period; and
      to receive and provide data indicating a change in a ventilation pressure during the observation period;
   a calculation and control unit configured:
      to determine local impedance values and impedance changes of at least one region of the lungs from the EIT data;
      to determine a data set with regional properties of the lungs, which indicates an indicator of compliance of the lungs, from the local impedances and local impedance changes, taking into account data that indicate a change in a ventilation pressure during the observation period;
      to analyze the data set with regional properties of the lungs based on a first comparison criterion to determine whether these properties indicate a hyperdistension of regional regions of the lungs;
      to generate and provide a regional hyperdistensions control signal, which represents the local regions of the lungs, with regional properties indicative of regional hyperdistensions;
      to analyze the data set with the regional properties of the lungs based on a second comparison criterion to determine whether these properties indicate a collapse of regional regions of the lungs; and
      to generate and provide a regional collapses control signal, which represents the local regions of the lungs, whose regional properties indicate regional collapses; and
   an output unit configured:
   to generate, provide or output an output signal using the regional hyperdistensions control signal and the regional collapses control signal, wherein the output signal represents a profile of properties for a visualization of local regions of the lungs, with regional properties showing deviations from the first comparison criterion or from the second comparison criterion.

2. A device in accordance with claim 1, wherein the calculation and control unit is further configured:
   to determine local impedance values and impedance changes of at least one region of the lungs from the EIT data; and
   to determine a tidal image with a current local distribution of the impedance values and impedance changes of the lungs from the local impedance values and local impedance changes and to generate and provide a tidal image control signal which is representative of the determined tidal image of the lungs.

3. A device in accordance with claim 2, in combination with a data output unit comprising with a component for graphic visualization that is arranged in or at or connected to the device for processing and visualizing EIT data, wherein the data output unit is configured to visualize the determined tidal image or the profile of properties or both the determined tidal image and the profile of properties with the use of the tidal image control signal or of the regional hyperdistensions control signal or of the regional collapses control signal or of the output signal or any combination of the tidal image control signal and the regional hyperdistensions control signal and the regional collapses control signal and the output signal.

4. A device in accordance with claim 1, in combination with a data output unit comprising with a component for graphic visualization that is arranged in or at or connected to the device for processing and visualizing EIT data, wherein the data output unit is configured to visualize the determined tidal image or the profile of properties or both the determined tidal image and the profile of properties with the use of the regional hyperdistensions control signal or of the regional collapses control signal or of the output signal or any combination of the regional hyperdistensions control signal and the regional collapses control signal and the output signal.

5. A device in accordance with claim 1, wherein values, which indicate positive end-expiratory pressure values, are determined during the observation period by the calculation and control unit based on the data that indicate a change in a ventilation pressure during the observation period data, which indicates measured pressure values of the ventilation course.

6. A device in accordance with claim 5, wherein data sets with maximum regional hyperdistensions are determined during the observation period by the calculation and control unit based on the regional properties, which indicate the compliance, and based on the data that indicate the measured pressure values of the ventilation course or based on the positive end-expiratory pressure values for a plurality of local lung regions or based on any combination of the regional properties, which indicate the compliance, and based on the data that indicate the measured pressure values of the ventilation course and based on the positive end-expiratory pressure values for a plurality of local lung regions.

7. A device in accordance with claim 1, wherein data sets with maximum regional hyperdistensions are determined during the observation period by the calculation and control unit based on the regional properties, which indicate the compliance, and based on the data that indicate a change in a ventilation pressure during the observation period data that indicate the measured pressure values of the ventilation course.

8. A device in accordance with claim 3, wherein the first comparison criterion is determined by the calculation and control unit during the observation period based on the data sets of maximum regional compliances and based on values which indicate positive end-expiratory pressure values.

9. A device in accordance with claim 5, wherein the first comparison criterion is determined by the calculation and control unit during the observation period based on the data sets of maximum regional compliances and based on the values which indicate positive end-expiratory pressure values.

10. A device in accordance with claim 3, wherein the second comparison criterion is determined by the calculation and control unit during the observation period based on the data sets of maximum regional compliances and values which indicate positive end-expiratory pressure values.

11. A device in accordance with claim 5, wherein the second comparison criterion is determined by the calculation and control unit during the observation period based on the data sets of maximum regional compliances and the values which indicate positive end-expiratory pressure values.

12. A device in accordance with claim 1, wherein the duration of at least two breathing cycles, with a respective inhalation time and expiration time each, is selected as the observation period.

13. A device in accordance with claim 1, wherein a duration of a maneuver, with changes in the ventilation pressure with a plurality of breathing cycles, with a respective inhalation phase and exhalation phase each, is selected as the observation period.

14. A device in accordance with claim 1, wherein a duration of a maneuver with changes in the ventilation pressure including a decremental or incremental PEEP trial with a plurality of breathing cycles, with a respective inhalation phase and exhalation phase each, is selected as the observation period.

15. A device in accordance with claim 1, wherein the data, which indicate a change in a ventilation pressure during the observation period, are provided by a ventilator or anesthesia apparatus.

16. A device in accordance with claim 1, wherein the device is configured as or is a part of a combination of devices carrying out a ventilation or carrying out an anesthesia or carrying out impedance tomography or carrying out any combination of a ventilation, an anesthesia and impedance tomography.

17. A device in accordance with claim 1, wherein the device is configured as or is a part of a combination of devices determining and visualizing properties of the lungs.

* * * * *